(12) United States Patent
Vishwanath (10) Patent No.: US 8,310,367 B1
(45) Date of Patent: Nov. 13, 2012

(54) METHODS OF IMPLANTING ELECTRONICS IN OBJECTS AND OBJECTS WITH IMPLANTED ELECTRONICS

(75) Inventor: Arkalgud Krishnamurthy Vishwanath, Karnataka (IN)

(73) Assignee: Empire Technology Development LLC, Wilmington, DE (US)

( * ) Notice: Subject to any disclaimer, the term of this patent is extended or adjusted under 35 U.S.C. 154(b) by 560 days.

(21) Appl. No.: 12/551,164

(22) Filed: Aug. 31, 2009

(30) Foreign Application Priority Data

May 18, 2009 (IN) .......................... 1143/CHE/2009

(51) Int. Cl.
  *G08B 13/14* (2006.01)
(52) U.S. Cl. .................. 340/572.1; 340/572.8
(58) Field of Classification Search ............... 340/572.1, 340/572.8; 29/825, 846
  See application file for complete search history.

(56) References Cited

U.S. PATENT DOCUMENTS

| | | |
|---|---|---|
| 4,910,417 A | 3/1990 | El Gamal et al. |
| 5,194,759 A | 3/1993 | El-Ayat et al. |
| 5,304,871 A | 4/1994 | Dharmarajan et al. |
| 5,347,519 A | 9/1994 | Cooke et al. |
| 5,448,187 A | 9/1995 | Kowalski |
| 5,469,077 A | 11/1995 | Cox |
| 5,469,109 A | 11/1995 | Paivinen |
| 5,477,167 A | 12/1995 | Chua |
| 5,495,181 A | 2/1996 | Kolze |
| 5,498,978 A | 3/1996 | Takahashi et al. |
| 5,498,979 A | 3/1996 | Parlour et al. |
| 5,534,793 A | 7/1996 | Nasserbakht |
| 5,552,720 A | 9/1996 | Lulla et al. |
| 5,566,107 A | 10/1996 | Gilliam |
| 5,712,577 A | 1/1998 | Cho |
| 6,687,131 B1 | 2/2004 | Miehling |
| 6,716,782 B2 | 4/2004 | Heng et al. |
| 2004/0238623 A1* | 12/2004 | Asp ........................... 340/572.8 |
| 2006/0267843 A1* | 11/2006 | Sakama et al. ......... 343/700 MS |
| 2007/0244470 A1* | 10/2007 | Barker et al. ..................... 606/1 |

FOREIGN PATENT DOCUMENTS

| | | |
|---|---|---|
| JP | 2004-240881 A | 8/2004 |
| WO | 2004102626 A2 | 11/2004 |

OTHER PUBLICATIONS

Machine translation of JP 2004-240881 A, issued Aug. 26, 2004.*
"Hitachi Unveils Smallest RFID Chip", RFID Journal, Mar. 14, 2003, pp. 1-4, obtained fron url: <http://www.rfidjournal.com/article/articleview/337/1/1/>.

(Continued)

*Primary Examiner* — Thomas Mullen
(74) *Attorney, Agent, or Firm* — Foley & Lardner LLP (57) ABSTRACT

Systems and methods including implanting RFID tags into metal-containing objects. The RFID tags are coated in a heat resistant coating. The surface of the metal-containing object could be heated and the coated RFID tag could be injected into the metal-containing object by allowing less heat to be transferred to the RFID electronics than an amount of heat to destroy the RFID electronics. The metal-containing objects can be monitored and tracked. Apparatus with implanted metal-containing objects can be remotely monitored and controlled.

24 Claims, 8 Drawing Sheets

OTHER PUBLICATIONS

Grossman, "Tag You're It", Time Magazine, Oct. 18, 2007, pp. 1-4, obtained fron url: <http://www.time.com/time/magazine/article/0,9171,1673283,00.html>.

Howard, "Beat the Heat", Boeing Frontiers, Integrated Defense Systems, Jun. 2006, vol. 5, Issue 2, pp. 1-3, obtained from url: <http://www.boeing.com/news/frontiers/archive/2006/june/i_ids2.html>.

"Protective Shuttle Tiles Insulate on Earth", Aerospace Technology Innovation, Sep./Oct. 1998, vol. 6, No. 5, pp. 1-3, obtained from url: <http://ipp.nasa.gov/innovation/Innovation65/protective.htm>.

International Search Report and Written Opinion for PCT International Patent Application No. PCT/IB2010/001122, mailed on Aug. 19, 2010.

* cited by examiner

METHODS OF IMPLANTING ELECTRONICS IN OBJECTS AND OBJECTS WITH IMPLANTED ELECTRONICS

RELATED APPLICATION

This application claims the benefit under 35 U.S.C. §119(a) of Indian Application No. 1143/CHE12009, which was filed on May 18, 2009, and is incorporated herein by reference in its entirety.

BACKGROUND

Radio frequency identification (RFID) tags were first used during World War II to help the military identify whether aircraft were friend or foe. In the late 1980s, the use of RFID tags increased significantly when they became the basis for electronic toll collection along the East Coast. In the late 1990's, interest in the use of RFID tags again increased significantly as corporations began investigating the use of RFID tags to track merchandise.

SUMMARY

Figures 1, 2:
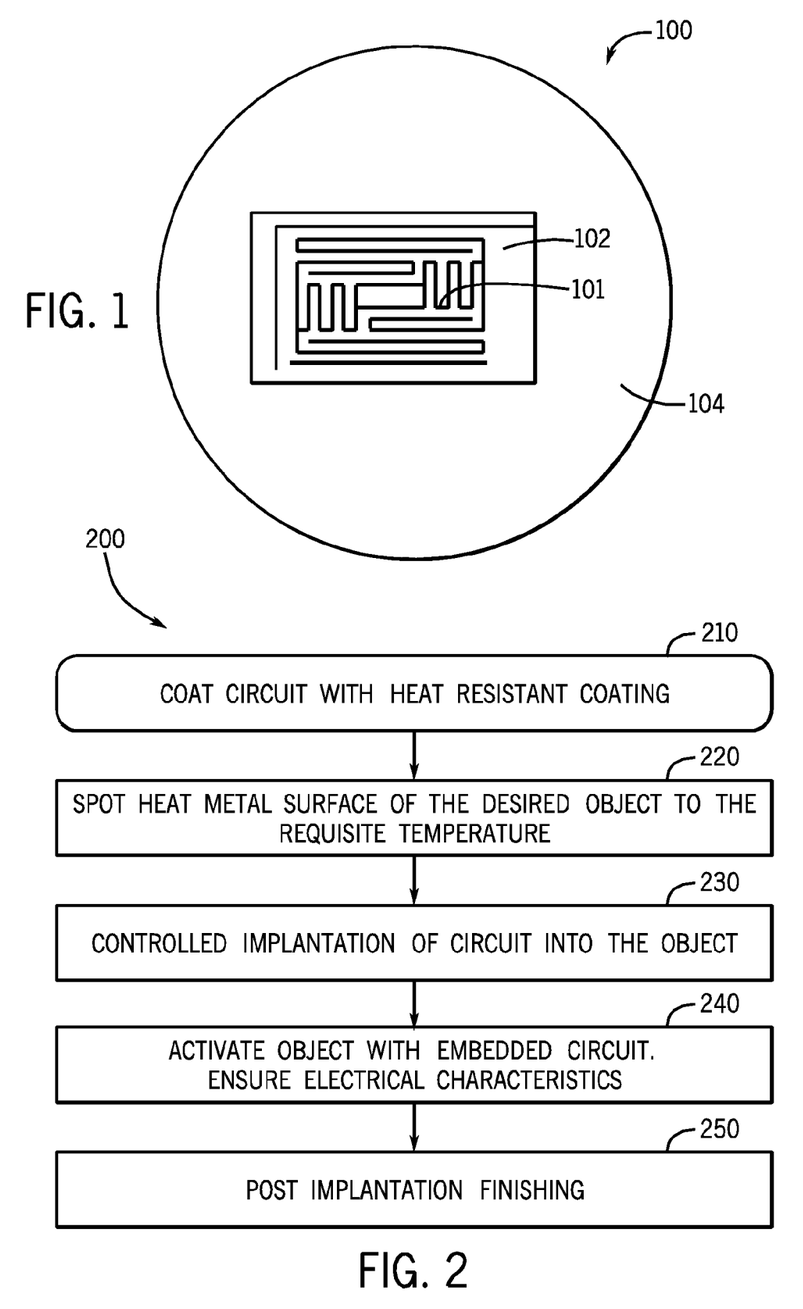
FIG. 1 is a schematic diagram of heat resistant coated RFID tag.
FIG. 2 is a flow diagram illustrating an embodiment of an implantation method.

An embodiment relates to a device comprising electronics encapsulated in a heat resistant coating, the heat resistant coating configured to protect the electronics from heat surrounding the electronics during implantation of the electronics in an object by allowing less heat to be transferred to the electronics than an amount of heat to destroy the electronics (FIG. 1). In one aspect, the object comprises metal. In another aspect, the electronics comprise a radio frequency identification (RFID) tag. The heat resistant coating may comprise amorphous silicon, SiN, $SiO_2$, $Al_2O_3$, $SiO_2$—$Al_2O_3$, or a borosilicate or any other suitable heat resistant material. In one aspect, the RFID tag comprises a passive, semi-passive, or active RFID tag.

Another embodiment relates to a method comprising encapsulating electronics in a heat resistant coating, heating an object, implanting the encapsulated electronics into the object, the heat resistant coating encapsulating the electronics configured to protect the electronics from heat surrounding the electronics during implantation of the electronics in the object by allowing less heat to be transferred to the electronics than an amount of heat to destroy the electronics (FIG. 2). In one aspect, the object comprises metal. In another aspect, the electronics comprise a radio frequency identification (RFID) tag. In another aspect, the heat resistant coating comprises amorphous silicon, SiN, $SiO_2$, $Al_2O_3$, $SiO_2$—$Al_2O_3$, or a borosilicate. A portion of the object may comprise a molten metal. Another aspect further comprises testing the RFID tag after implanting. Another aspect further comprises performing post implantation finishing on the object after said implanting. In another aspect, post implantation finishing includes one or more of annealing, grinding, polishing, peening, painting or varnishing. Another aspect, further comprises reforming a surface of the object.

Figure 4:
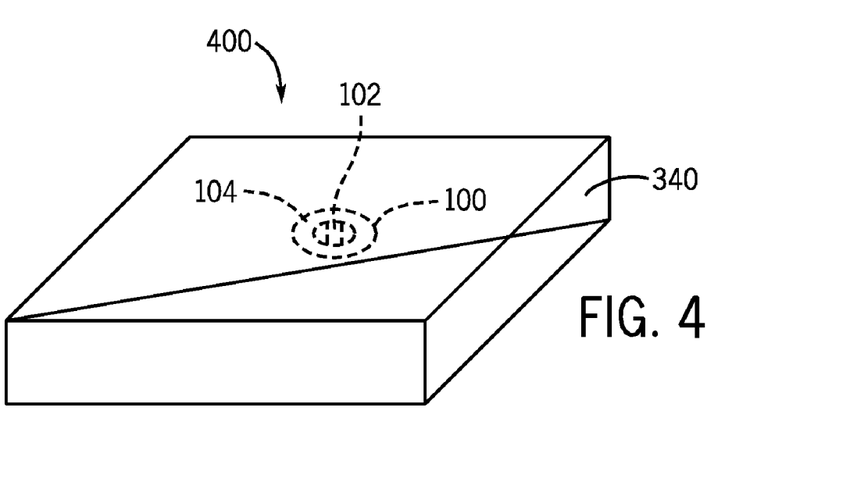
FIG. 4 is a schematic diagram of an object having an implanted RFID tag of an embodiment.

Another embodiment relates to an object comprising an embedded electronic circuit, the electronic circuit encapsulated in a heat resistant coating, the heat resistant coating configured to protect the electronic circuit from heat surrounding the electronic circuit during implantation of the electronic circuit in the object by allowing less heat to be transferred to the electronic circuit than an amount of heat to destroy the electronic circuit (FIG. 4). In an aspect, the electronic circuit comprises a radio frequency identification (RFID) tag. In another aspect, the object comprises metal. In another aspect, the RFID tag comprises a passive, semi-passive, or active RFID tag. In another aspect, the metal comprises an essentially pure elemental metal, a metal alloy, or a metal matrix composite. In another aspect, the object comprises lead, aluminum, iron, steel, nickel, titanium, or carbon. In another aspect, the heat resistant coating comprises amorphous silicon, SiN, $SiO_2$, $Al_2O_3$, $SiO_2$—$Al_2O_3$, or a borosilicate.

In another aspect, the embedded electronic circuit provides intelligence to the object by providing information regarding the relative motion of the object. In another aspect, the relative motion comprises rotation or vibration. In still another aspect, the object is configured for remote surgery, manipulation of robots, manipulation of manufacturing machines, or prosthetics.

Figure 3:
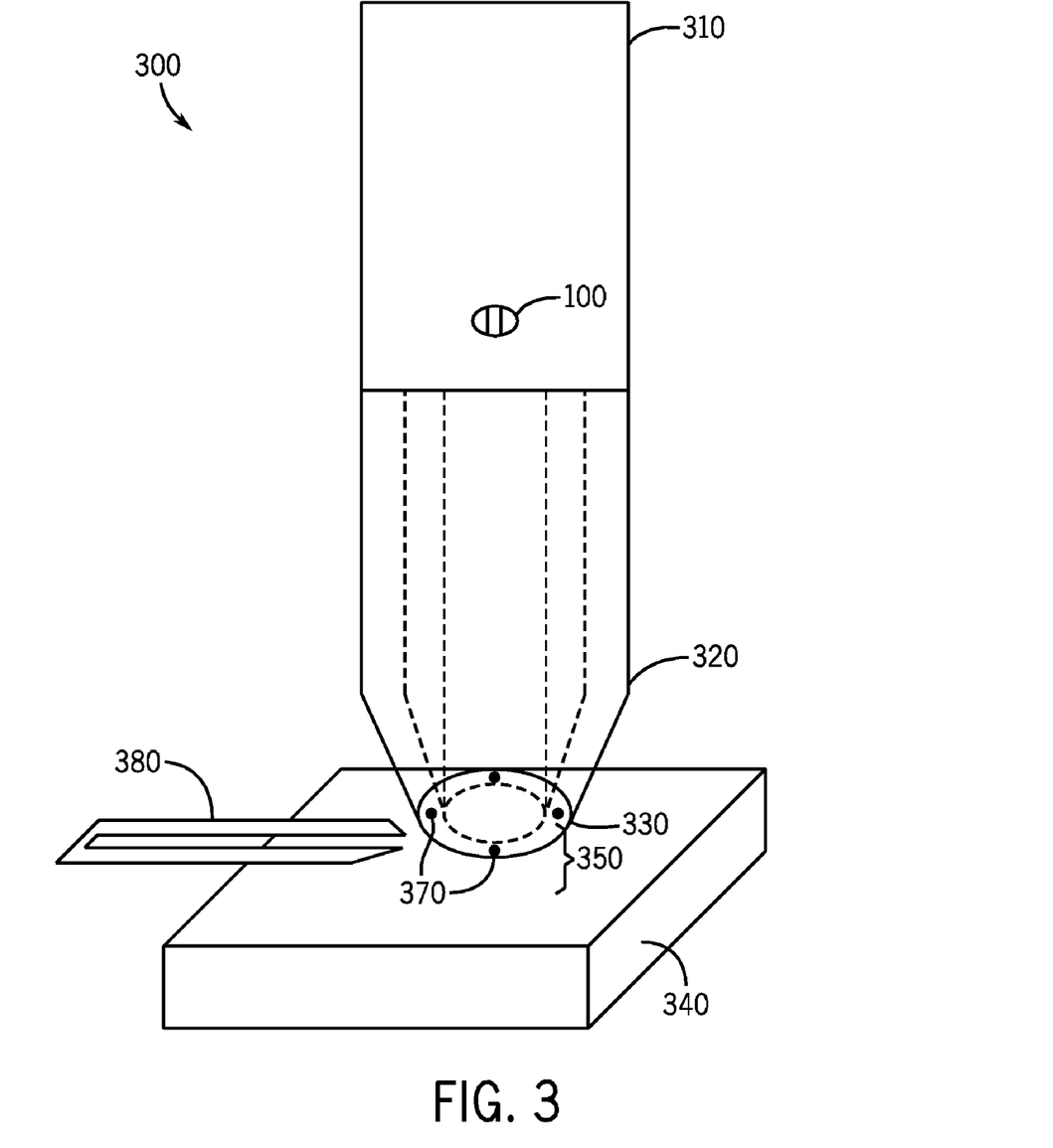
FIG. 3 is a schematic diagram of an implantation device of an embodiment.

Another embodiment relates to an apparatus comprising a plurality of objects, at least one of the plurality of objects comprising a an electronic circuit encapsulated in a heat resistant coating, the heat resistant coating encapsulating the electronic circuit configured to protect the electronic circuit from heat surrounding the electronic circuit during implantation of the electronic circuit in the at least one of the plurality of object by allowing less heat to be transferred to the electronic circuit than an amount of heat to destroy the electronic circuit (FIG. 3). In an aspect, the electronic circuit can comprise a radio frequency identification (RFID) tag. In another aspect, the RFID tag comprises a tag from Class I, Class II, Class III, or Class IV. In another aspect, the apparatus comprises a plurality of electronic circuits. In another aspect, the apparatus comprises a plurality of RFID tags. In another aspect, the plurality of RFID tags comprises more than one class.

Another embodiment relates to a method comprising monitoring electronics embedded in an object of an apparatus, the electronics being encapsulated in a heat resistant coating configured to protect the electronics from heat surrounding the electronics during implantation of the electronics in an object by allowing less heat to be transferred to the electronics than an amount of heat to destroy the electronics. In an aspect, the electronics comprise a radio frequency identification (RFID) tag. In another aspect, the RFID tag comprises a transponder. Another aspect further comprises monitoring a relative turn or location of a first part of the apparatus relative to a second part of the apparatus. Another aspect further comprises monitoring parameters adapted to assist in maintenance/servicing of the apparatus. Another aspect further comprises monitoring a plurality of RFID tags in the apparatus. Another aspect further comprises remotely controlling the apparatus.

Another embodiment relates to an apparatus comprising an implantation device configured to implant an electronic circuit embedded in an object, the electronic circuit encapsulated in a heat resistant coating configured to protect the electronic circuit from heat surrounding the electronic circuit during implantation of the electronic circuit tag in the object; an injection nozzle and at least one heat source. In an aspect, the at least one heat source is located in the nozzle. In another aspect, the heat source comprises an electron beam, a laser, an infrared source, a plasma source, or an electric arc. In another aspect, the implantation device comprises mechanical, pneumatic, or electric potential.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

As used in the specification and claims, the singular forms "a", "an" and "the" include plural references unless the context clearly dictates otherwise. A thing followed by the term "containing" such as "metal-containing" refers something that at least contains that thing but could also contain other things. Thus, the term "metal-containing" refers to something that at least contains a metal therein.

As will be discussed in more detail below, electronics such as RFID tags can be implanted safely in a non-destructive way in an object whose surface can be softened or melted by the application of heat. In the description below, the implanted electronics are illustrated by way of RFID tags. RFID tags, however, are but one example of an electronic circuit which may be implanted. Implanted circuits may include various sensors such as temperature, vibration, heat, as well as control circuitry and memory. Further, in many of the examples below, the object to be implanted comprises a metal or is metal-containing. However, the object may be made of plastic or a carbon composite material or a composite of metal and non-metal.

In one embodiment, the RFID tags can be first built into a heat resistant coating to form a RFID tag encapsulated in a heat resistant coating (also referred to herein as "RFID tag-in-shell" and "coated RFID tag"), which could be then implanted into the metal. The term "heat resistant coating" refers to a coating around the RFID tag that protects the RFID electronics from the heat surrounding the RFID tag during implantation of the RFID tag in a metal-containing object by allowing less heat to be transferred to the RFID electronics than an amount of heat to destroy the RFID electronics. The metal-containing object may comprise a substantially pure elemental metal, a metal alloy, or even a metal matrix composite. Metals which may be implanted include, but are not limited to, lead, aluminum, iron and steel, nickel, and titanium. The RFID tag can be built-in during metal molding, that is, as the metal component could be formed or after any step of fabrication. Further, the metal-containing object may be subject to further fabrication and/or finishing steps after implantation. Typically, the RFID tag could be encapsulated in a ceramic material or heat insulating semiconductor material.

The thickness of the ceramic material or heat insulating semiconductor material should be of a thickness sufficient to protect the RFID tag electronics. That is, the thickness of the ceramic material or heat insulating semiconductor material should be sufficient enough to prevent the temperature of the electronics from rising to a level that would destroy them. The appropriate thickness is a function of the thermal conductivity of the ceramic material or heat insulating semiconductor material and the temperature gradient. This can be computed by the following equation:

$$q = -k\nabla T$$

Where q is the heat, k is the thermal conductivity and $\nabla T$ is the thermal gradient. The thickness may also be determined with thermal diffusivity ("α") data. Where the thermal diffusivity is the ratio of thermal conductivity to the volumetric heat capacity:

$$\alpha = k/\rho c_p$$

Where k is the thermal conductivity, p is the density of the material and $c_p$ is the specific heat capacity of the material. Thus, given the heat inputted (which can be predetermined or determined experimentally) to soften or melt the surface of the metal-containing object, the temperatures of the metal surface and the coated RFID tag, and the thermal conductivity or thermal diffusivity of the coating material, the thickness of the desired coating can be determined.

The following tables provide sample thermal conductivity and thermal diffusivity data which may be used to calculate coating thicknesses. This data is merely illustrative. References with thermal conductivity and thermal diffusivity data are widely available.

TABLE I

| Substance | Thermal conductivity (cal/sec/cm/K) |
| --- | --- |
| Brick (Common red) | 0.0015 |
| Concrete (Stone) | 0.0022 |
| Glass (soda) | 0.0017 |
| Sand (dry) | 0.00093 |

TABLE II

| Substance | Thermal diffusivity (M²/sec) |
|---|---|
| Aluminum oxide (polycrystalline) | $1.2 \times 10^{-5}$ |
| Common brick | $5.2 \times 10^{-7}$ |
| Window glass | $3.4 \times 10^{-7}$ |
| Sandstone | $1.12 \times 10^{-6}$ to $1.19 \times 10^{-6}$ |

Typically, the coated RFID tag will be at room temperature while the melted portion metal-containing object is at its melting temperature. The melting temperature of several illustrative metals is provided in Table III below.

TABLE III

| Elements | Symbol | Melting Point Celsius | Melting Point Fahrenheit |
|---|---|---|---|
| Aluminum | Al | 659 | 1218 |
| Brass (85 Cu 15 Zn) | Cu + Zn | 900-940 | 1652-1724 |
| Bronze (90 Cu 10 Sn) | Cu + Sn | 850-1000 | 1562-832 |
| Cast Iron | C + Si + Mn + Fe | 1260 | 2300 |
| Carbon | C | 3600 | 6512 |
| Chromium | Cr | 1615 | 3034 |
| Copper | Cu | 1083 | 1981 |
| Gold | Au | 1063 | 1946 |
| Hydrogen | H | −259 | −434.2 |
| Inconel | Ni + Cr + Fe | 1393 | 2540 |
| Iron | Fe | 1530 | 2786 |
| Lead | Pb | 327 | 621 |
| Magnesium | Mg | 670 | 1240 |
| Manganese | Mn | 1260 | 2300 |
| Monel | Ni + Cu + Si | 1301 | 2400 |
| Nickel | Ni | 1452 | 2646 |
| Phosphorous | P | 44 | 111 |
| Silicon | Si | 1420 | 2588 |
| Silver | Ag | 961 | 1762 |
| Stainless Steel | Cr + Ni + Mn + C | 1363 | 2550 |
| Steel-High Carbon | Cr + Ni + Mn + C | 1353 | 2500 |
| Medium Carbon | Cr + Ni + Mn + C | 1427 | 2600 |
| Low Carbon | Cr + Ni + Mn + C | 1464 | 2700 |
| Tin | Sn | 232 | 450 |
| Titanium | Ti | 1795 | 3263 |
| Tungsten | W | 3000 | 5432 |
| Zinc | Zn | 419 | 786 |

In some embodiments of the invention, to further reduce the possibility of damage to the RFID electronics, cooling is applied to the surface of the metal-containing object after implantation. Cooling may be accomplished, for example, through the use of forced cool air. In other embodiments, heat sinks or fins are contacted with or affixed to the metal-containing object.

The operating limits of many common electronics is about 45° C.-60° C. For some electronics, the range can be stretched to about 85° C. Beyond this, their working is not guaranteed. There are, however, special purpose electronics which have been developed to withstand higher temperatures. Indeed, electronics have been developed to operate in a range of −40° C.-300° C.

In some embodiments, the shape of the coated RFID tag is designed to reduce splash during implantation. The time for the molten or softened material to re-harden is a function of the material. That is, it is a function of the heat capacity of the material as well as the volume of the material. The time to re-harden determines the time window for implantation. The time window ($t_w$) may be described as a function of thermal mobility ($\mu_{th}$) and diffusion constant (D) of the cooling material:

$$\lim_{T_{soft} \to T_{hard}} F\{\mu_{th} D\}$$

The relationship between thermal mobility ($\mu_{th}$) and diffusion constant (D) may be described by the Einstein kinetic relationship:

$$D = \mu k_B T$$

Where kB is Boltzmann's constant and T is the temperature of the material.

The energy for implantation may be determined empirically for each material to be implanted. The energy is related to the size of the gap between the injection nozzle and the surface of the object to be implanted. The energy is also a function of the velocity of the injected coated RFID tag. That is, a higher velocity results in a higher implantation energy and vice versa. High energy, high velocity coated RFID tags will penetrate deeper than low energy, low velocity coated RFID tags.

In general, the desired depth of penetration will vary with the material of the object to be penetrated. The optimal depth for each material can be determined empirically. Parameters to consider when determining the optimal depth include having enough material to protect the implanted RFID tag and the quality of the signal received from the implanted RFID tag. The maximum depth for a material is a function of the loss of fluidity as a function of time and the depth of fluidity as a function of the heat source. That is, materials which cool slowly will typically allow deeper penetration because there is more time for the coated RFID tag to penetrate. Further, higher power heat sources will make deeper pools than lower power heat sources.

In some embodiments, the encapsulating material could be similar to or same as a tile material used in the Space Shuttle. In one embodiment, the RFID tag-in-shell could be impregnated into the metal object using spot-heating and ballistic implantation. The heat resistant coating protects the RFID electronics from the heat of the hot metal and heat generated during implantation. In some embodiments, a small spot on a metal containing object is heated until it is molten, facilitating implantation of the RFID tag-in-shell within the molten metal. In other embodiments, it would be sufficient to heat the metal until soft. The choice of whether to melt or soften the metal may depend on the desired depth of implantation, the alloy, and the final use of the metal containing object.

The RFID tags of the various embodiments include a transponder. A transponder could be a receiver-transmitter that will generate a reply signal upon proper electronic interrogation.

RFID tags may be passive, semi-passive, or active. Active RFID uses an internal power source, such as a battery, within the tag to continuously power the tag and its RF communication circuitry. Active RFID allows extremely low-level RF signals to be received by the tag (since the reader/interrogator does not power the tag), and the tag can generate high-level signals back to the reader/interrogator. Active RFID tags are continuously powered, whether in the reader/interrogator field or not, and are normally used when a longer tag read distance could be desired. Active RFID tags can typically be read from distances of approximately 300 feet.

Passive RFID relies on RF energy transferred from the reader/interrogator to the tag to power the RFID tag. Passive RFID tags reflect energy from the reader/interrogator or receive and temporarily store a small amount of energy from the reader/interrogator signal in order to generate the tag response. Passive RFID generally has stronger RF signals from the reader/interrogator relative to active RFID. Further, the RF signal strength returned from the tag could be constrained to relatively low levels by the limited energy. Passive RFID tags are best used when the tag and interrogator will be close to one another. Passive RFID tags can typically be read from distances of approximately 30 feet.

Semi-passive RFID uses an internal power source to monitor environmental conditions, with RF energy transferred from the reader/interrogator similar to passive tags to power a tag response. Semi-passive RFID tags use a process to generate a tag response similar to that of passive tags. Semi-passive RFID tags differ from passive RFID tags in that semi passive tags possess an internal power source (battery) for the tag's circuitry which allows the tag to complete other functions such as monitoring of environmental conditions (temperature, shock) and which may extend the tag signal range.

Currently, there are four general classes of RFID tags. The various embodiments may use RFID tags from one or more of these classes. Class I tags are passive. These tags generally include a unique identifier number, a "kill" function to disable the tag, and are typically memory programmable only once. Newer generation of Class I devices, however, may be rewritable and password protected. Class II tags are also passive and generally have extended identification numbers, include additional memory, are rewritable, and include password protection. Class III tags are semi-passive. Class III tags are similar to Class II tags but also include a power source and one or more sensors. Class IV tags are active. Class IV devices include a power source and are capable of initiating communications with a reader/interrogator or another RFID tag.

RFID tags could be as small as 0.3 mm$^2$ or even smaller. The size of the RFID tag, however, is not limiting. That is, the size of the RFID tag may be selected depending on the configuration of the part which is implanted and the use of the RFID tag.

The use of embedded electronics, especially embedded RFID tags, turns ordinary metallic objects into intelligent objects. The intelligence is added to the object by providing information regarding the relative motion of the object. In this manner, the motion of the intelligent object can be precisely monitored and the intelligent object adjusted. The relative motion may be rotation or vibration. Uses of intelligent metal objects include, but are not limited to, remote surgery, manipulation of robots, manipulation of manufacturing machines, and prosthetics. This also helps convert passive objects into active objects that can communicate to a computer or with other active objects. In an automobile, for example, active components can communicate to a central computer. These examples and others are described in more detail below.

FIG. 1 illustrates a heat resistant coated RFID tag 100 according to one embodiment. The heat resistant coated RFID tag 100 could comprise a RFID tag 102 having RFID electronics 101, and a heat resistant coating 104 encapsulating the RFID tag 102.

The RFID tag 102 may be passive, semi-passive, or active. The heat resistant coating 104 may be a ceramic or a heat insulating semiconductor material. Suitable ceramic materials include, but are not limited to, SiN, $SiO_2$, $Al_2O_3$, $SiO_2$—$Al_2O_3$, and borosilicates. Heat insulating semiconductor materials may include for example amorphous silicon. The coating material may be selected based on the desired properties of the heat resistant coating 104 such as the temperature to be withstood, and the desired strength of the heat resistant coating 104. It is desirable that the coating material be sufficiently stable and heat resistant to protect the encapsulated RFID tag 102.

Coating the RFID tag 102 with the heat resistant coating 104 may be accomplished through a variety of processes. One process, for example, could comprise encapsulation. Encapsulation may be accomplished by dip coating. In the dip coating process the RFID tag could be immersed in a tank containing the coating material, removed from the tank, and allowed to dry. The coated piece may be also be dried by force-drying or baking. Another method of coating could be the spin coating process. In the spin coating process, excess amount of a coating solution could be placed on the RFID tag 102, which could be then rotated at high speed in order to spread the fluid by centrifugal force. Another method of coating could be sputtering. Sputtering is a process whereby atoms of the coating are ejected from a solid target material due to bombardment of the target by energetic ions. That is, a target which could comprise the coating material could be bombarded with high energy particles. The high energy particles erode the target, the atoms of which fly to the RFID tag 102 and stick. Still another method of coating includes blow molding a shell and inserting the RFID tag within. This method could be similar to glass blowing in bulb formation. Further, the coating can be done as an extended step in RFID packaging wherein coating is grown or deposited over and/or around the RFID tag as allowed by the process technology. Many other coating processes can be used. For example, a specialized semiconductor processing packaging step to completely cover the RFID on all sides to form encapsulation may be used. A coating method fis sufficient if it can encapsulate the RFID tag without damaging the electronics.

FIG. 2 is a flow diagram illustrating a method of manufacturing a metal containing object containing a coated RFID tag according to one embodiment. Process flow 200 includes steps of: coating the RFID tag with a heat resistant coating 210, spot heating the surface of a metal-containing object to be implanted 220, and implanting the coated RFID tag into the metal-containing object 230. The method also includes optional steps of testing the electrical characteristics of the implanted RFID tag 240 and post implantation finishing steps 250.

The step of spot heating the surface of a metal-containing object to be implanted 220 may also be accomplished through a variety of methods. In some embodiments, the metal surface could be heated with an electron beam. In other embodiments, the metal surface could be heated with a laser, plasma, or infrared source. Indeed, any directed heat source could be used. The metal surface may also be heated with an electric arc. Typically, the metal surface is heated until the surface metal is molten.

In other embodiments, the surface could be heated until softened rather than melted. Softening for many materials occurs at ½ the homologous temperature, $T_H$. The homologous temperature $T_H$ is defined as $T/T_M$, where $T_M$ is the melting temperature of the alloy. In modern superalloys, softening generally occurs at temperatures approaching $0.9T_M$.

The step of implanting the coated RFID tag into the metal-containing object 230 may also be performed in a variety of methods. In one embodiment, the coated RFID tag 100 could be accelerated pneumatically and implanted into the surface. In other embodiments, the outer surface of the heat resistant coating 104 could be provided with a charge and the coated RFID tag 100 could be implanted in a manner similar to ion implantation. That is, an electric potential could be generated between the surface of the part and the implantation device which causes the charged coated RFID tag 100 to accelerate to the surface. In still other embodiments, the coated RFID tag 100 could be mechanically injected into the metal-containing object with a hypodermic needle. In still anther method, a cavity could be micro-machined into the metal-containing object, the coated RFID tag 100 deposited, and the surface of the object reformed. The surface of the object may be reformed, for example, by spot melting the surface and allowing molten metal to flow into the machined cavity, covering the coated RFID tag 100. Further, in another method, a modified gun can shoot the coated RFID tag onto the soft metal surface. The choice of implantation method and/or equipment mayor may not vary depending on the material being implanted and may also be selected based on equipment availability, cost, part configuration or other parameters as desired by the user.

The step of testing the electrical characteristics of the implanted RFID tag 240 may include one or more tests. The tests may include, for example, charging a passive RFID device 102 and attempting to read its identification number. Optional post implantation finishing steps 250 may include annealing the surface of the implanted object, grinding, polishing, or peening the surface. Other optional steps include painting or varnishing the surface. In one aspect, implantation produces essentially no damage to the surface. In this way, evidence of the implanted RFID tag is essentially invisible to the casual observer.

FIG. 3 is a schematic diagram of an implantation apparatus 300 according to one embodiment. The apparatus 300 of this embodiment includes an implantation gun mechanism 310, and a nozzle 320 having a nozzle tip 330. In one aspect, the nozzle 320 could comprise a ceramic material. In other aspects, however, the nozzle could comprise one or more metals. In some embodiments, the nozzle 320 includes one or more heat sources 370. As discussed above, the heat sources 370 may includes lasers, infrared sources, or electron beam sources. The heat sources 370 may also include an electrode adapted for arc heating. The apparatus 300 may also include one or more external heat sources 380. The external heat sources 380 may comprise lasers, infrared sources, plasma sources, electron beam sources, or electrodes for arc heating. In some embodiments, a gap 350 between the nozzle tip 330 and the metal object 340 could be maintained when heating and injecting the coated RFID tag 100 into the metal object 340. In some embodiments, implantation may be accomplished through the nozzle 320.

The size of the gap 350 is generally a function of several parameters. These parameters include whether the injection chamber (not shown) is sealed or open. If sealed, whether the chamber is evacuated or if the chamber includes an inert atmosphere. Further, the coated RFID tag 100 may be implanted along with other material, such as a filler. The filler may be liquid or solid. Additionally, the coated RFID tag 100 may be implanted along with a gaseous material.

FIG. 4 is a schematic diagram of an implanted object 400 of another embodiment. The implanted object 400 could comprise one more coated RFID tags 100 implanted in a metal object 340. As illustrated, the metal object 340 could be a block. As described below in more detail, however, the metal object 340 may be of any configuration and may be a component of a machine. Further, multiple coated RFID tags 100 may be implanted in the same metal object 340. In this manner, different portions of the same metal object 340 may be independently monitored. In one aspect, monitoring may be accomplished, for example, with ultra short range RFID.

Illustrative Examples

Embodiments include many useful methods and devices. For example, in one embodiment, implantation of a coated RFID tag in metal-containing components allows for the tracking of the individual metal-containing components of an apparatus comprising a plurality of metal-containing objects, as well as the apparatus itself. Individual metal-containing components can be inventoried prior to assembly and monitored at each stage during shipping in a manner similar to which non-metal packages are currently monitored by commercial shipping companies. Further, once an apparatus could be assembled using components containing the coated RFID tags, one, several, or all of the coated RFID tags 100 can be monitored to track the movements of the apparatus. Further, in an apparatus comprising several tagged metal-containing components, the apparatus can be monitored to determine if any of the metal-containing components were replaced.

Figure 5:
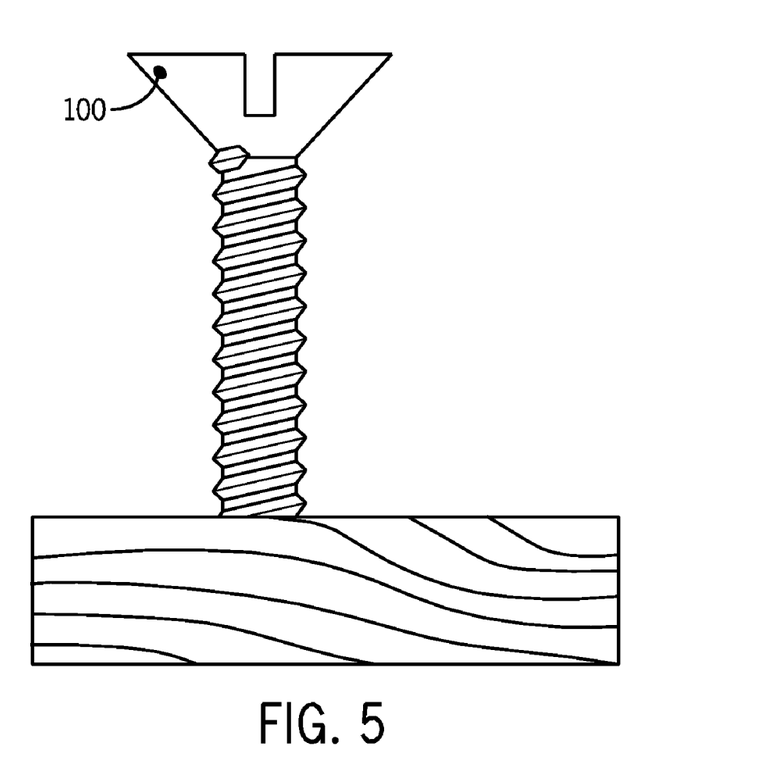
FIG. 5 is a schematic illustration of an embodiment comprising a coated RFID tag embedded in a screw.

Another embodiment could comprise the monitoring of the relative turn or a location measure for fixtures such as screws, and nut and bolts (FIG. 5). A coated RFID tag 100 may be, for example, implanted in the head of a screw. An RFID monitor may then be configured to monitor the rotation of the screw in a manner similar to monitoring the rotation of a tire on a car or bicycle. In this way, passive components may be turned into intelligent components.

Figure 6:
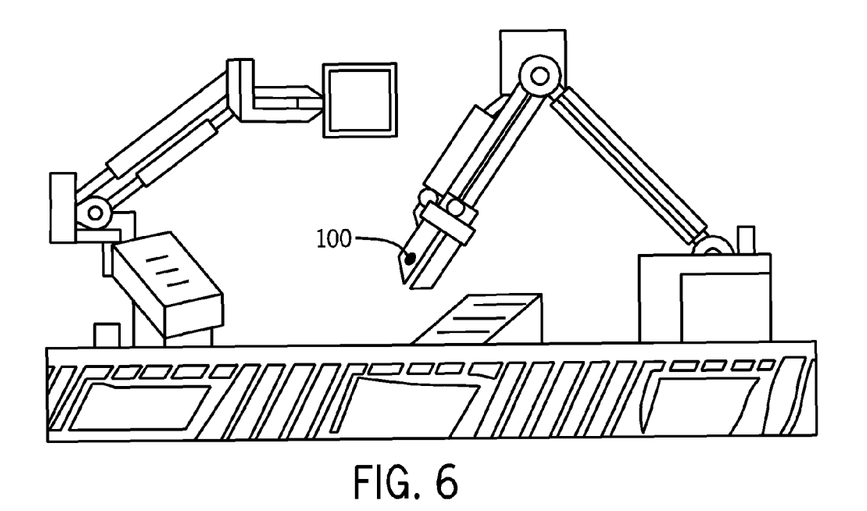
FIG. 6 is a schematic illustration of an embodiment comprising a coated RFID tag embedded in a robot.

Other embodiments include, timing and sequencing in manufacturing assembly. For example, with RFID tags 100 located in moving parts and other RFID tags 100 (and/or RFID monitors) located in stationary parts, the relative motion of the moving parts can be precisely determined and monitored (FIG. 6). This embodiment could be similar to the last embodiment, however, it allows for sophisticated monitoring and control of apparatuses with moving parts.

Figure 7:
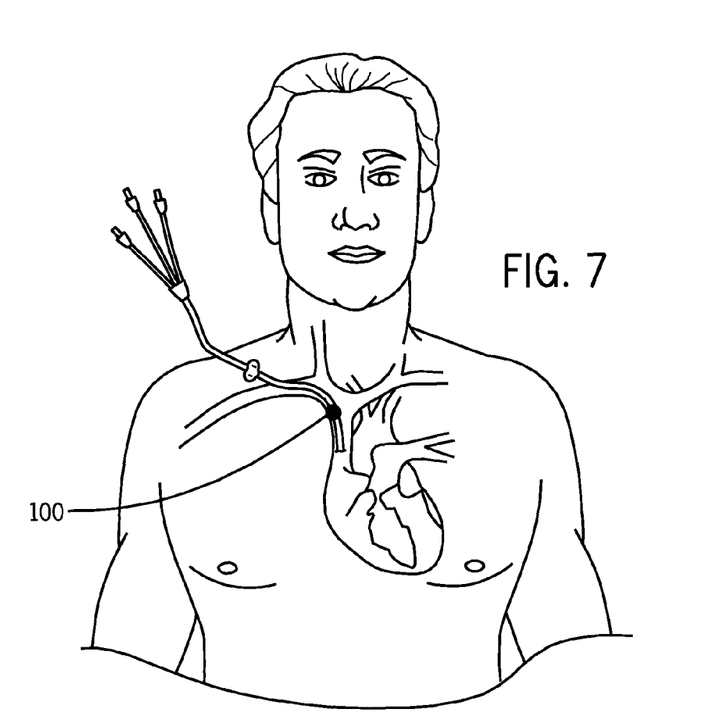
FIG. 7 is a schematic illustration of an embodiment comprising a coated RFID tag embedded in a surgical instrument.

Still other embodiments include remote surgery with intelligent components (FIG. 7). That is, the use of information from precisely located RFID tags can be used to monitor and guide remote surgical tools. Thus, rather than rely on the conventional optical techniques now in use, this embodiment allows for the use of precision RFID technology for monitoring and control of remote medical devices.

Figure 8:
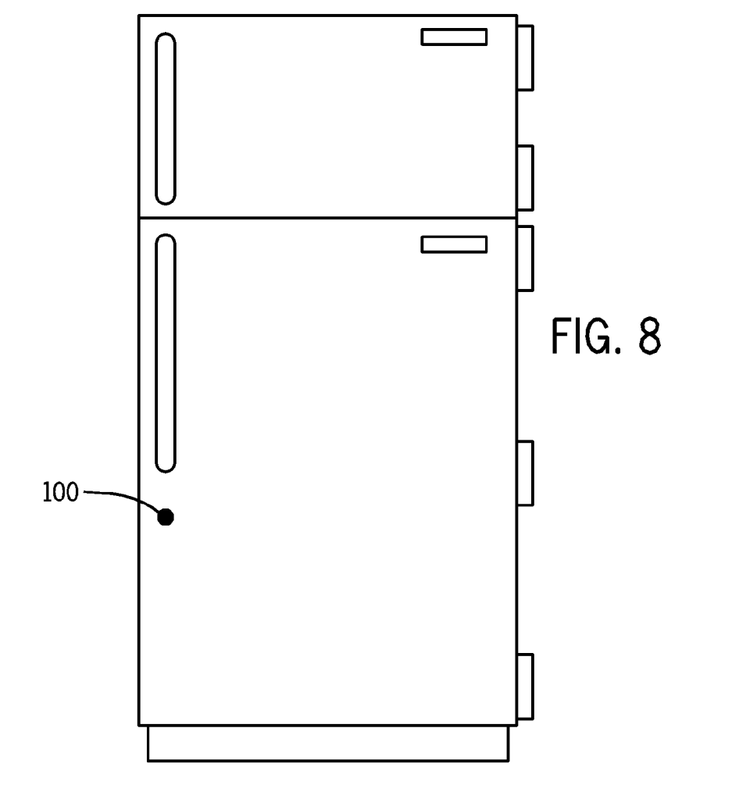
FIG. 8 is a schematic illustration of an embodiment comprising a coated RFID tag embedded in a white good (refrigerator).

In still another embodiment, remote diagnostics of equipment, especially consumer household white goods can be monitored (FIG. 8). White goods are generally major household appliances and include, but are not limited to, air conditioners, dishwashers, clothes dryers, freezers, refrigerators, ranges, stoves, ovens, water heaters, washing machines, trash compactors, and microwave ovens. In one example, active RFID tags 100 with temperature sensors are embedded in a freezer or refrigerator can be used to diagnose whether coolant needs to be added. In another embodiment, embedded RFID tags 100 with vibration sensors are monitored to determine if the motor of the appliance could be going bad and needs to be replaced. In this way, the service requirements may be determined before a technician could be sent to the house. This may lead to greater efficiency. For example, the technician may know in advance whether a part needs to be replaced and order the part before going to the consumer's house. This embodiment may also be used for "brown goods." Brown goods are typically small household electrical entertainment appliances such as: CD and DVD players, televisions, camcorders, still cameras, video game consoles, HiFi and home cinema, telephones, and answering machines.

Figure 9:
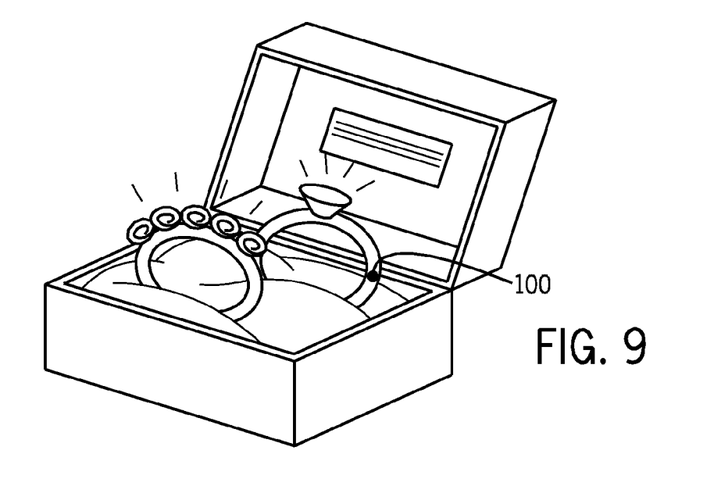
FIG. 9 is a schematic illustration of an embodiment comprising a coated RFID tag embedded in jewelry.

In another embodiment, the authenticity and warranty management of high value items, for example, jewelry can be improved. In this embodiment, coated RFID tags 100 with unique identification codes can be safely implanted into items such as jewelry without causing noticeable damage to the implanted object (FIG. 9). Indeed, post implantation finishing can remove substantially all visible traces of the implantation process. In one example, if a consumer gives her jewelry to a jeweler for cleaning and suspects she received a substitute in return, she can have the jewelry scanned. Failure to yield the proper identification could be evidence of substitution. For greater security, encryption may be incorporated in the RFID tag 102. In addition, it may provide a means for built-in authenticity, jeweler's stamp of originality, year of purchase, the value at a given time, etc.

Figure 10:
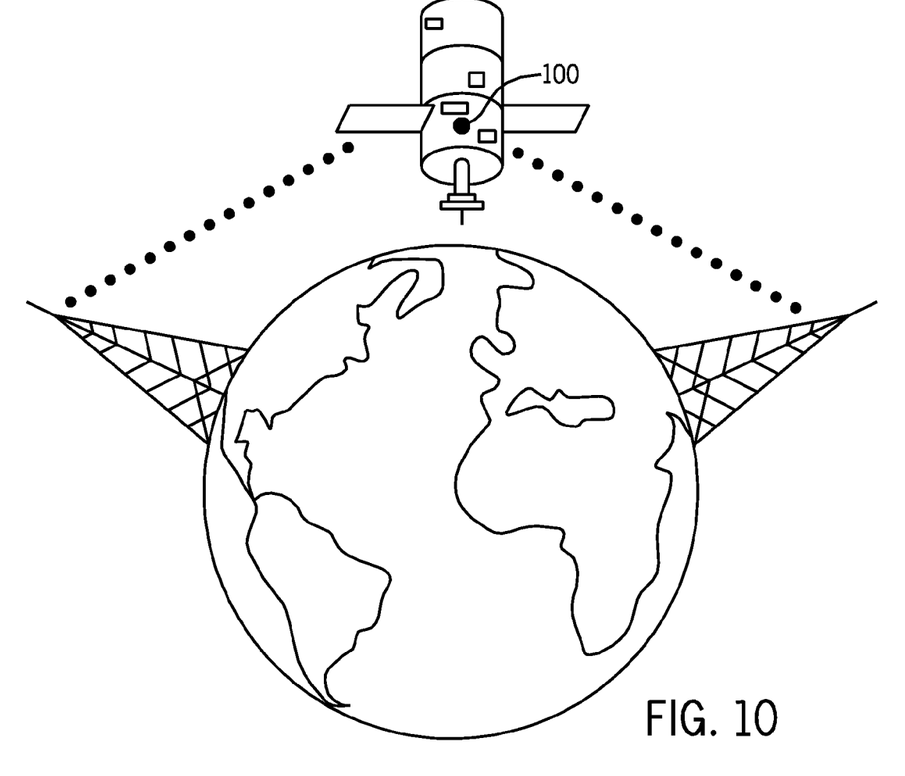
FIG. 10 is a schematic illustration of an embodiment comprising a coated RFID tag embedded in a satellite.

Another embodiment could comprise a method of deploying and managing spacecraft/satellites (FIG. 10). Typically, unmanned missions are operated by preprogrammed instructions. Although some correction could be possible, currently there could be limited sensor data and control. With implanted coated RFID tags 100 in certain parts, however, precise monitoring and control could be possible. In one aspect, multiple coated RFID tags 100 can communicate with each other as well as the reader/interrogator.

In another embodiment, multiple communicating embedded coated RFID tags 100 are used in robots (FIG. 6). Multiple coated RFID tags 100 can be implanted in both the moving parts and in stationary parts of the robot. By monitoring the relative motions of the moving parts of the robot, the robots can be controlled or pre-programmed. Further, coated RFID tags 100 can be implanted in components to be acted upon by the robot. In this manner, the position of the robot relative to the part can be closely monitored. This may be advantageous for example, for a robot used to paint automobile doors. The motion of the robot can be monitored and the distance between the robot and the part can also be monitored and adjusted as desired.

Figure 11:
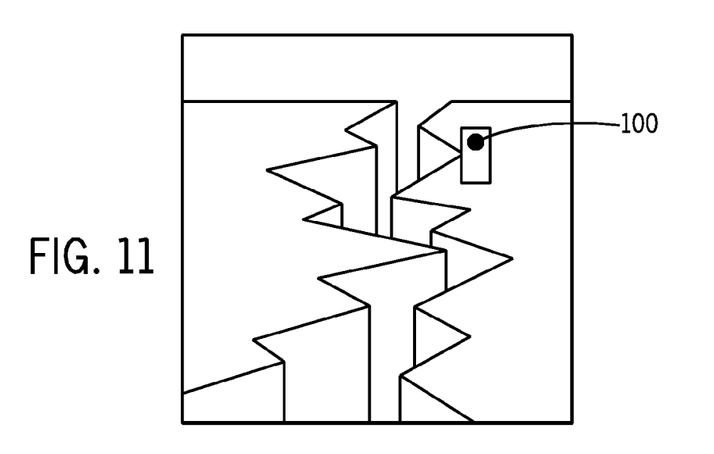
FIG. 11 is a schematic illustration of an embodiment comprising a coated RFID tag configured to detect vibration (earthquake).

In still another embodiment, the motion of metal-containing components due to vibration could be monitored (FIG. 11). In this embodiment sensitive motion sensors, such as accelerometers, can be incorporated in a coated active RFID tag 100 and embedded in a metal object 340. This embodiment may be used to monitor vibration sensitive apparatus such as airplane engines. It can also be used to measure earthquakes by monitoring the vibration of an apparatus and subtracting its normal or background vibration. Indeed, vibration monitoring from several sources in an effected area can be correlated to help determine the epicenter and the magnitude of an earthquake.

In another embodiment, material handling by robots becomes easier (FIG. 6). In building construction, routine labor oriented can be passed to robots as intelligent materials can be made available. In this manner, many building construction works can be automated. Another embodiment enables measurement of stress or fatigue of a part or between parts in safety/critical environments such as aircraft. Availability of intelligent parts helps gather better data during normal operation or during abnormal conditions such as an aircraft crash. Another embodiment includes gathering better data of collisions conducted in research laboratories, that is artificial collision or impact. Another embodiment enables monitoring tools in factory floors or points of assembly such as during space walk.

Another embodiment could comprise an alloy material database which includes data for controlling the implantation equipment. The database may include actual experimental data and interpolated data. It may also include data generated from computer models. The database may include, but is not limited to, data concerning melting temperature, heat capacity, and material strength. The database can be used, for example, to manage the thermal sources, to adjust the size of the gap 250, and the implantation velocity of the coated RFID tag 100.

Figure 12:
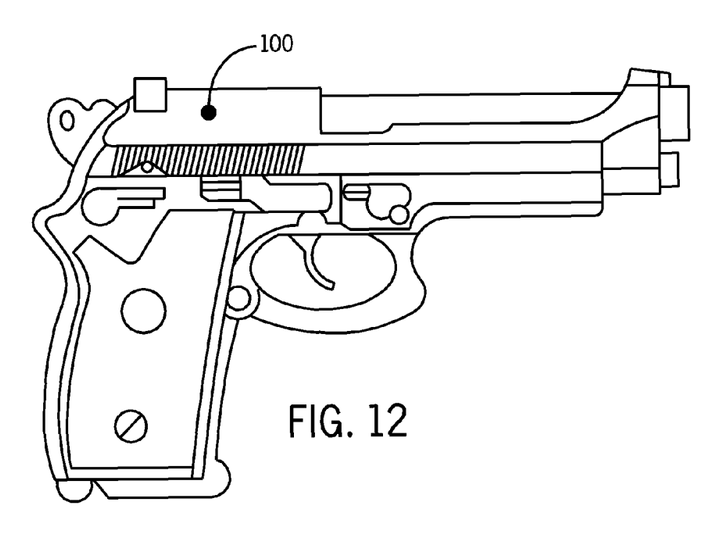
FIG. 12 is a schematic illustration of an embodiment comprising a coated RFID tag embedded in a firearm.

In another embodiment, arms and ammunitions can be tracked (FIG. 12). Currently, serial numbers can be easily erased, scratched or disfigured. Implanted RFID tags, however, are harder to find and easy to track. Indeed, with implanted RFID tags, movement of arms and ammunition can be remotely monitored and even be monitored within a building. RFID readers can be placed at every door and window in the factory or warehouse if desired.

Figure 13:
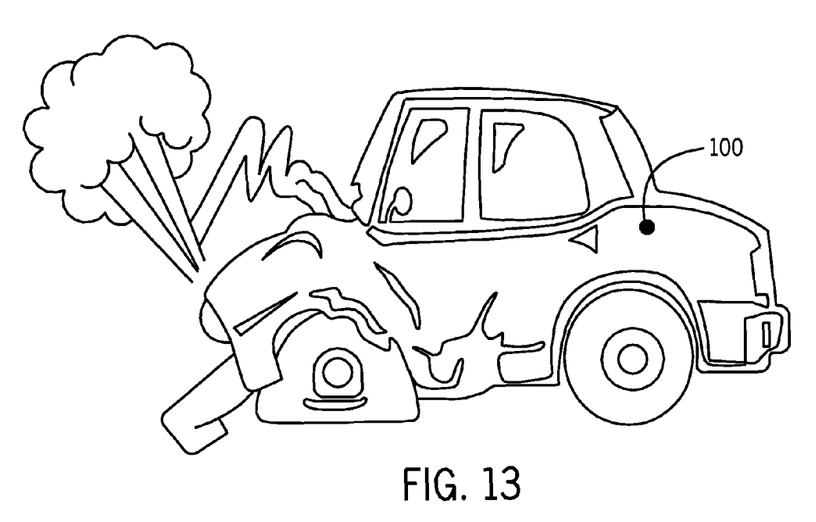
FIG. 13 is a schematic illustration of an embodiment comprising a coated RFID tag embedded in a vehicle.

Another embodiment could comprise a method of vehicle service management (FIG. 13). The owner of the vehicle can be given parts data that can be monitored by a database maintained by the car owner. In this way, the owner can monitor the replacement and service record of various parts of the vehicle. This embodiment can further be used to verify the service record of a used car. In one aspect, the database may be incorporated in an onboard computer in the vehicle. Indeed, this technology may even solve one part of Game Theory puzzle—The Game of Incomplete Information. That is, this technology provides a means to verify & validate a transaction, especially in $2^{nd}$ car sales.

Figure 14:
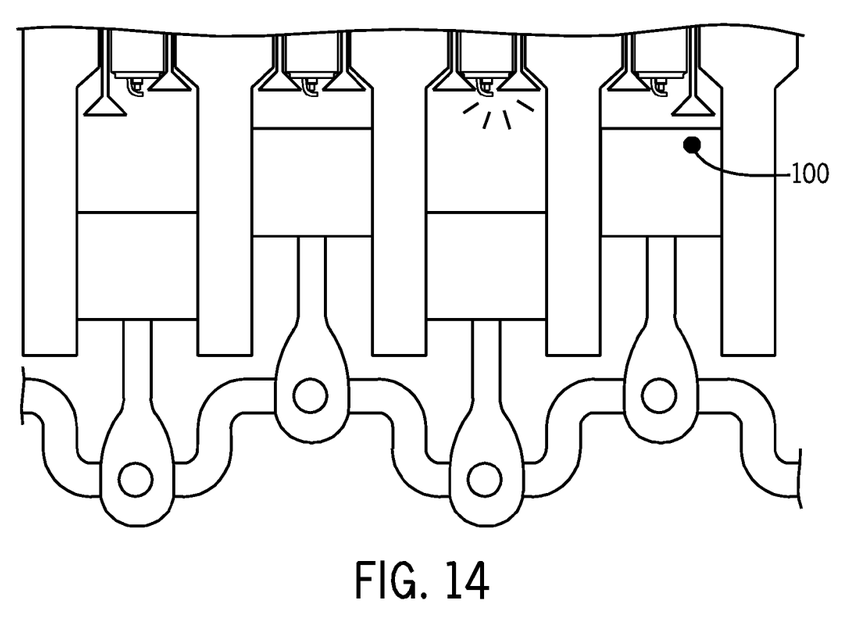
FIG. 14 is a schematic illustration of an embodiment comprising a coated RFID tag embedded in an engine.

In another embodiment, implanted RFID tags implanted in an automobile work in conjunction with servos in the engine, making it possible to remotely freeze the engine (FIG. 14). This embodiment may be advantageous, for example, in a crime scenario. In another aspect of this embodiment, the vehicle may be monitored for moving violations such as speeding, passing through a red light, moving past a stop sign without stopping, or trespassing.

Figure 15:
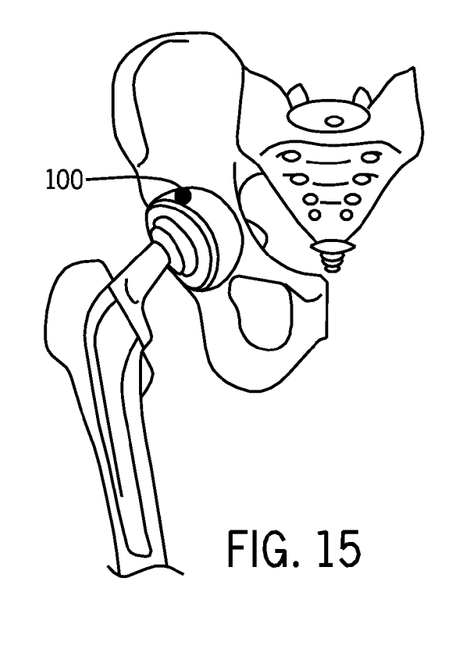
FIG. 15 is a schematic illustration of an embodiment comprising a coated RFID tag embedded in a medical implant.

In another embodiment, RFID tags and/or sensors are implanted in human prosthetics or implants to provide intelligent prosthetics or implants (FIG. 15). In another embodiment, RFID tags and/or sensors are implanted in the tips of welding torches leading to improved precision in welding. In another embodiment, implanted RFID tags and/or sensors are used to detect power outages.

The foregoing detailed description has set forth various embodiments of the devices and/or processes via the use of diagrams, flowcharts, and/or examples. Insofar as such diagrams, flowcharts, and/or examples contain one or more functions and/or operations, it will be understood by those within the art that each function and/or operation within such diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to optical coupling to permit transmission of optical light, for example via an optical pipe or fiber, physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.).

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All references cited herein, including but not limited to patents, patent applications, and non-patent literature are hereby incorporated by reference herein in their entirety.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method comprising:
   encapsulating electronics in a heat resistant coating;
   heating an object so as to cause at least a portion of a surface of the object to become softened;
   implanting the encapsulated electronics into the object via the softened surface,
   the heat resistant coating encapsulating the electronics configured to protect the electronics from heat during implantation of the electronics in the object by allowing less heat to be transferred from the softened surface to the electronics than an amount of heat to destroy the electronics; and performing post-implantation processing of the object, the post-implantation processing including at least one of annealing, grinding, polishing, peening, painting and varnishing.

2. The method of claim 1, wherein the object comprises metal.

3. The method of claim 2, wherein at least a portion of the softened surface comprises a molten metal.

4. The method of claim 1, wherein the electronics comprise a radio frequency identification (RFID) tag.

5. The method of claim 4, further comprising testing the RFID tag after said implanting.

6. The method of claim 1, wherein the heat resistant coating comprises amorphous silicon, SiN, $SiO_2$, $Al_2O_3$, $SiO_2$—$Al_2O_3$, or a borosilicate.

7. The method of claim 1, wherein encapsulating the electronics comprises dip coating the electronics in the heat resistant coating.

8. The method of claim 1, wherein encapsulating the electronics comprises sputtering the heat resistant coating onto the electronics.

9. The method of claim 1, wherein heating the surface of the object comprises heating at least a portion of the object to at least one-half the melting temperature of the object.

10. The method of claim 1, wherein heating the surface of the object comprises irradiating the surface of the object with at least one of an electron beam, a laser beam, infrared radiation, a plasma, and an electrical arc.

11. The method of claim 1, wherein implanting the encapsulated electronics comprises ejecting the encapsulated electronics from a nozzle into the object.

12. The method of claim 1, wherein implanting the encapsulated electronics comprises pneumatically accelerating the encapsulated electronics towards the softened surface of the object.

13. The method of claim 1, wherein implanting the encapsulated electronics comprises:
applying an electric charge to at least one of the encapsulated electronics and the softened surface of the object; and
generating an electric potential between the encapsulated electronics and the softened surface of the object.

14. The method of claim 1, further comprising:
determining an implantation energy required to implant the encapsulated electronics to a desired depth below the surface of the object.

15. The method of claim 1, wherein the object comprises at least one of an air conditioner, a dishwasher, a clothes dryer, a freezer, a refrigerator, a range, a stove, an oven, a water heater, a washing machine, a trash compactor, and a microwave oven.

16. A method comprising:
encapsulating electronics in a heat resistant coating;
heating an object so as to cause at least a portion of a surface of the object to become softened;
implanting the encapsulated electronics into the object via the softened surface, the heat resistant coating encapsulating the electronics configured to protect the electronics from heat surrounding the electronics during implantation of the electronics into the object by allowing less heat to be transferred to the electronics from the softened surface than an amount of heat to destroy the electronics; and
reforming the surface of the object after implanting the encapsulated electronics into the object.

17. The method of claim 16, wherein reforming the surface of the object comprises spot melting at least a portion of the surface of the object.

18. An object comprising:
metal; and
an electronic circuit encapsulated in a heat resistant coating and embedded in the metal, the heat resistant coating configured to protect the electronic circuit from heat surrounding the electronic circuit during implantation of the electronic circuit in the metal by allowing less heat to be transferred to the electronic circuit than an amount of heat to destroy the electronic circuit.

19. The object of claim 18, wherein the electronic circuit comprises a radio frequency identification (RFID) tag.

20. The object of claim 19, wherein the RFID tag comprises a passive, semi-passive, or active RFID tag.

21. The object of claim 18, wherein the metal comprises at least one of lead, aluminum, iron, titanium, or carbon.

22. The object of claim 21, wherein the metal comprises an essentially pure metal, a metal alloy, or a metal composite.

23. The object of claim 18, wherein the object is seamless.

24. The object of claim 18, wherein the object comprises at least one of an air conditioner, a dishwasher, a clothes dryer, a freezer, a refrigerator, a range, a stove, an oven, a water heater, a washing machine, a trash compactor, and a microwave oven.

* * * * *

UNITED STATES PATENT AND TRADEMARK OFFICE
CERTIFICATE OF CORRECTION

PATENT NO. : 8,310,367 B1
APPLICATION NO. : 12/551164
DATED : November 13, 2012
INVENTOR(S) : Vishwanath Arkalgud Krishnamurthy It is certified that error appears in the above-identified patent and that said Letters Patent is hereby corrected as shown below:

On the Title page of the patent, please replace section (12) with the following corrected version:

-- (12) United States Patent
~~Vishwanath~~ Arkalgud Krishnamurthy --

On the Title page of the patent, please replace section (75) with the following corrected version:

-- (75) Inventor: ~~Arkalgud Krishnamurthy~~ Vishwanath Arkalgud Krishnamurthy, Karnataka (IN) --

Signed and Sealed this
Nineteenth Day of February, 2013

Teresa Stanek Rea
*Acting Director of the United States Patent and Trademark Office*

UNITED STATES PATENT AND TRADEMARK OFFICE
CERTIFICATE OF CORRECTION

PATENT NO. : 8,310,367 B1
APPLICATION NO. : 12/551164
DATED : November 13, 2012
INVENTOR(S) : Vishwanath It is certified that error appears in the above-identified patent and that said Letters Patent is hereby corrected as shown below:

On the Title Page, in Field (56), under "OTHER PUBLICATIONS", in Column 2, Line 3, delete "fron" and insert -- from --, therefor.

Title Page 2, in Field (56), under "OTHER PUBLICATIONS", in Column 1, Line 2, delete "fron" and insert -- from --, therefor.

In Column 1, Line 8, delete "1143/CHE12009," and insert -- 1143/CHE/2009, --, therefor.

In Column 4, in Table I, below "Substance" Line 2, delete "(Stone" and insert -- (Stone) --, therefor.

In Column 8, Line 31, delete "fis" and insert -- is --, therefor.

In Column 9, Line 3, delete "anther" and insert -- another --, therefor.

In Column 9, Line 11, delete "mayor" and insert -- may or --, therefor.

In Column 10, Line 17, delete "tum" and insert -- turn --, therefor.

In Column 13, Lines 22-23, delete space between "devices," and "such".

Signed and Sealed this
Nineteenth Day of March, 2013

Teresa Stanek Rea
*Acting Director of the United States Patent and Trademark Office*